United States Patent [19]

Oppenheim et al.

[11] 4,107,288

[45] Aug. 15, 1978

[54] INJECTABLE COMPOSITIONS, NANOPARTICLES USEFUL THEREIN, AND PROCESS OF MANUFACTURING SAME

[75] Inventors: Richard Charles Oppenheim, Parkville; Jennifer Joy Marty, East Kew, both of Australia; Peter Speiser, Zurich, Switzerland

[73] Assignee: Pharmaceutical Society of Victoria, Parkville, Australia

[21] Appl. No.: 611,835

[22] Filed: Sep. 9, 1975

[30] Foreign Application Priority Data

Sep. 18, 1974 [AU] Australia .............................. 8951/74

[51] Int. Cl.$^2$ .......................... A61K 9/66; A61K 9/64
[52] U.S. Cl. ...................................... 424/22; 252/316; 424/34; 424/35; 424/36; 424/37; 424/214; 424/230; 424/244; 424/254

[58] Field of Search .................... 252/316; 424/36, 37, 424/19, 22

[56] References Cited

U.S. PATENT DOCUMENTS

| | | | |
|---|---|---|---|
| 3,242,051 | 3/1966 | Hiestand et al. ................... | 424/33 X |
| 3,436,355 | 4/1969 | Bakan .................................. | 252/316 |
| 3,447,945 | 6/1969 | Mishima et al. .................. | 252/316 X |
| 3,565,559 | 2/1971 | Sato et al. ........................ | 252/316 X |

*Primary Examiner*—Richard D. Lovering
*Attorney, Agent, or Firm*—Cushman, Darby & Cushman

[57] ABSTRACT

Particles in the size range from about 10 to about 1000 nm, preferably less than about 500 nm, which comprise a crosslinked matrix of macromolecules of natural origin.

A biologically or pharmacodynamically active material may be supported on or incorporated into the matrix.

18 Claims, No Drawings

INJECTABLE COMPOSITIONS, NANOPARTICLES USEFUL THEREIN, AND PROCESS OF MANUFACTURING SAME

The present invention is concerned with particles which are suspendible in fluid media together with methods for their production and application.

The production and application of microcapsules containing liquid or solid substances for medical and technical use, such as, for example, administration through the skin or mucous membranes, for masking the flavour of bitter drugs, coatings resistant to gastric juice, for the protection of active substances against environmental influences, or for the capsulation of adhesive substances which can be activated by pressure or temperature, for the manufacture of application forms of pesticides with a depot effect and for the capsulation of dyes, are well known. The shell material of these microcapsules consists mainly of polymeric, more or less water-soluble material such as gelatin or synthetic polymers. Microencapsulation can be performed by building up the envelope in rotating drums, plates, discs, rollers, or other mechanical means and by fluidization or spray condensation.

A method commonly used at present is so-called "simple" or "complex" coacervation (J. Pharm. Sc., 59, 1367 (1970), which is a process generally comprising four stages:

(a) Production of an emulsion or suspension of the enclosure substance in a suitable liquid excipient which already contains the wall material in solution.

(b) Production of the wall material in the form of small droplets in this suspension or emulsion by phase separation or the addition of a further phase, a three-phase system being formed in the appropriate circumstances.

(c) Capsulation of the enclosure phase by the droplets of wall phase material separated in b).

(d) Solidification of the at first still liquid wall of the capsule.

Stirring must be continued during the whole process in order to maintain the stability of the multi-phase system. The size of the microcapsules produced by these methods varies between a minimum diameter of a few micrometers (1 micrometer = $10^{-6}$ meters) and several hundred micrometers, and may be as much as several millimeters.

The use of such microcapsules in medicine is limited to oral, cutaneous, epithelial and enteral administration. An object of the present invention is to obviate the substantial limitations thus imposed upon the medical applications of microcapsules.

In order to ensure safe parenteral administration (including the intravenous route) of such particles the diameter of the particles must be reduced from the range of a few micrometers up to several hundred micrometers to a range of a few nanometers (1 nanometer = $10^{-9}$ meters) up to several hundred nanometers. This is a 100- to 10,000-fold reduction in size from the known microcapsules.

Furthermore, parenteral administration requires that the product must have low toxicity and high biodegradability and the synthetic polymers of the prior art are not generally satisfactory in this regard.

Accordingly, in one aspect, the present invention provides particles in the size range from about 10 to about 1000 nm, preferably less than about 500 nm, which particles comprise a crosslinked matrix of macromolecules of natural origin.

Typical natural macromolecules include, for example, gums, soluble celluloses or proteins like gelatin or albumin.

In another aspect, the present invention provides a method of manufacturing particles in the size range from about 10 to about 1000 nm, preferably less than about 500 nm, which particles comprise a crosslinked matrix of macromolecules of natural origin, which method comprises:

(a) solvating the macromolecule to form a thermally equilibrated clear solution;

(b) treating said solution with a desolvating agent until the macromolecule has reached the desolvation region (as hereinafter defined);

(c) adding a hardening agent to the mixture;

The principal advantage of the method according to the invention reside mainly in the fact that, in contrast to known methods, a product is obtained which comprises particles which are 100 to 10,000 times smaller than the known microcapsules. As a rule their diameter is less than 1000 nm and mainly under 500 nm. Such particles are referred to herein as "nanoparticles".

Preferably the particles comprise a biologically or pharmodynamically active material supported on or incorporated into the crosslinked matrix. Such an active material may be incorporated into the particles at any convenient date in their manufacture or may be added to the particles at a later stage.

The particles obtained with their enclosed and adsorbed active material are consequently colloid soluble in water. This opens up entirely new opportunities for application. More especially this method allows biologically and pharmaco-dynamically active material to be administered without hazard — including intravenous injection where appropriate — since a greater or lesser portion of the active substance is enclosed and adsorbed in the structure of the particles with a greater or lesser degree of fixity or is partly free, depending on the quantitive ratio between the excipient and the active substance. There is thus a possibility of carrying out selective long-term therapy in which the organism has to tolerate only a minimum of biologically or pharmaco-dynamically active substance.

The point at which the active material if any is added in the method depends on the nature of the active material. Furthermore, not every active material, for example protein, drug, pesticide, fertilizer or dye, is suitable for incorporation in the particles obtained according to the invention.

Substances having colloidal solubility properties and which are at least colloid water-soluble or organic-soluble are generally suitable as the macromolecular component.

The term "macromolecule of natural origin" as used herein will be understood to include macromolecules which, although originally of natural origin, have been chemically modified to some extent, e.g., as in the case of cellulose which has been alkylated or otherwise modified.

The nature of the solvent for the natural macromolecule is important as the solvent must be able to solvate the macromolecule thus causing the macromolecular chain to be extended and discrete. Examples of suitable solvents for various natural macromolecules are listed below.

| Natural Macromolecule | Solvent |
| --- | --- |
| Gelatin | water, glycerol |
| Serum albumin | water |
| Collagen | water |
| Casein | water |
| Insulin | solutions of alkali hydroxides |
| Gum arabic | water |
| Water soluble celluloses e.g. carboxymethyl cellulose | water |
| Rosin | alcohols, solutions of alkali hydroxides |
| Water insoluble celluloses e.g. ethylcellulose | benzene, alcohols |
| Mixtures like gelatin/insulin | water |
| Zein | mixtures of: acetone-water alcohol water glycols |

Suitable desolvation agents for solvated macromolecules are well known in the microencapsulation art wherein a proteinaceous coacervative (such as gelatin) is deposited around solid particles of active ingredients. Suitable desolvating agents are known from the microencapsulation art and are for example polyvalent anions, such as for example $SO_4^{--}$, or polyvalent cations such as for example $Ca^{++}$, $Mg^{++}$, and alcohols such as for example ethanol and isopropanol.

By the term "desolvation region" we mean conditions under which the macromolecule is partially desolvated by addition of other ingredients which preferably interact with the solvent molecules to the solution of the macromolecule. This region may be recognized by an increase in the intensity of scattered light. (Huglin M.B. ed. "Light scattering from polymer solutions", Ch. 15, 16, 17 Academic Press London & New York 1972). This increase in intensity is due to the macromolecules "rolling up" as the solvating molecules are removed from the intimate environment of the macromolecule.

The desolvation region may be determined for example by using a nephelometer or alternatively by observing the intensity of scattered light visually through a microscope.

After the desolvation region is reached, if further desolvating agent is added the intensity of scattered light increases rapidly and the solution becomes turbid. Care must therefore be taken not to overshoot the desolvation point, that is the point at which there is a marked increase in the intensity of the scattered light. If the point is overshot the mixture can be treated with a small amount of a less efficient solvating agent such as alcohol, for example, isopropanol or ethanol which will reverse the desolvation.

Hence alcohols can be used to generate the desolvating conditions or to reverse a situation in which the desolvation point has been overshot by the excess addition of other more active desolvating agents.

The active material if any is conveniently added in the alcohol under either of the above two situations.

The nature of the macromolecule is very important in determining the physical properties of the particles obtained in our invention. The most preferred macromolecular material of use in our invention is gelatin and the invention will now be described with particular reference to the use of gelatin as the macromolecular material. However those skilled in the art will be able to see how the information on gelatin may be modified for other proteins such as serum albumin, casein, collagen, as well as other natural macromolecules.

As the temperature of the system of gelatin and water rises, the strength of the interaction between the gelatin and the water will decrease, as more energy is stored in the bond. Desolvation of the gelatin involves the breaking of this gelatin-water bond. Hence it might be expected that an increase in temperature will assist in the production of nanoparticles. However, an increase in temperature also causes an increase in the rate of the hardening reaction and an increase in the rate of diffusion of one gelatin molecule towards another.

Preferably, the method of our invention is carried out at a temperature in the range from 10° to 100° C.

The behaviour of polar macromolecules such as proteins is greatly affected by the pH of the system. The charge on such molecules is determined by the pH of the system and the isoelectric point of the macromolecule. The use of suitably charged macromolecules facilitates the incorporation of oppositely charged active ingredients into the particles. The presence of a charge in the macromolecules can also aid in preventing formation of large aggregates.

A surfactant or suspending agent is normally added to the reaction mixture to act as a solubilizing or suspending agent for any water-insoluble active ingredients and as a wetting agent to facilitate dispersion of the final product in water.

The nature of the surfactant or suspending agent is not critical except that the surfactant or suspending agent should remain in solution throughout the process.

The effect of the hardening agent is to cause cross-linking of the macromolecule. Suitable crosslinking agents will be obvious to those skilled in the art. For gelatin the hardening agent is preferably an aldehyde for example formaldehyde or a dialdehyde, such as glutaraldehyde. Glutaraldehyde is far more efficient and the electron microscope pictures show that better smaller "particles" are formed using glutaraldehyde. Subject to efficient removal of excess glutaraldehyde, it is advantageous to use an excess of hardener. The excess hardener is preferably removed by chemical reaction. Methods for the removal of aldehyde are well known to those skilled in the art. A typical method is to react the excess aldehyde with a sulphite.

Aldehydes also have the advantage of substantially reducing the bacterial count in the sample.

There are several criteria which will determine the choice of the drug to be incorporated into the nanoparticles of the invention. Some of these criteria are those for any sustained release preparation; others are specific for the dose form of gelatin nanoparticles.

(1) The active ingredient will usually be one which is required to be used over a wide period of time and has to be administered often. Steroids are a typical example.

(2) The drug will need to have a therapeutic range which could be effectively released slowly and evenly from gelatin nanoparticles. A large dosage regime would exclude the possibility of using that drug.

(3) The drug must be chemically compatible with the manufacturing process. It must physically or chemically bind onto the particle, but be able to be released at the appropriate time; it must not react with, for example, the —CHO moiety of the hardening agent.

Typical drugs for use in our invention are phenobarbitone, diazepam, prednisolone phosphate, sodium salicylate, steroids, antidepressants, atropine, hormones and prostaglandins.

The invention has been described with particular reference to the use of the particles for the treatment of animals and humans preferably by injection, and in one specific aspect the invention provides injectable compositions comprising the particles of the invention in a fluid carrier.

The invention, however, is in no way limited to particles suitable for pharmaceutical use or to injectable compositions. Other uses for the particles include formulations of pesticides, insect hormones and attractants and for formulation of additives such as for example corrosion inhibitors and industrial bactericides, fungicides, stimulants, etc.

The invention is illustrated by, but by no means limited to, the following examples.

EXAMPLE 1

An aqueous solution of 20% w/v $Na_2SO_4$ was added slowly with stirring to 5.0 ml of a 2% w/v aqueous solution of gelatin until a rise in scattered light intensity occurred as measured on a nephelometer (approximately after addition of 4.5 ml of 20% w/v $Na_2SO_4$). A solution of 25 mg phenobarbitone in 1 ml of isopropanol was added slowly to the stirred mixture. 0.4 ml of a 25% glutaraldehyde solution was then added and the system left for 30 minutes. The product was dialysed using cellophane tubing and the product freeze dried. The product was examined under the electron microscope and was found to comprise quasispherical balls of diameter in the range from 200–400 nanometers.

EXAMPLE 2

Example 1 was repeated except that an additional 1.0 ml of isopropanol was added after the phenobarbitone solution. Similar results were obtained in Example 1 except that the "balls" tended to be slightly smaller in size.

EXAMPLE 3

An aqueous solution of 95% v/v ethanol was added slowly with stirring to 5.0 ml of a 2% w/v aqueous solution of gelatin until a rise in scattered light intensity occurred (approx. after addition of 4.0 ml ethanol). A solution of 25 mg of phenobarbitone in 1 ml 95% w/w ethanol was added to the stirred mixture. After dialysis and freeze drying as in Example 1, a similar product was obtained to the preceding Examples.

EXAMPLE 4

An aqueous solution of 5% w/v phenobarbitone in 95% v/v ethanol was added to a stirred solution of 5.0 ml of 2% w/v aqueous solution of gelatin until a rise in scattered light occurred (approximately after addition of 5 ml of phenobarbitone solution). The mixture was worked up as in preceding examples to give similar results.

EXAMPLE 5

An aqueous solution of 50% w/v ammonium sulphate was added slowly with stirring to 5 mls of an aqueous solution containing 5% w/v of human serum albumin and 1% of w/v of sodium salicylate until a rise in light intensity occurred as measured on a nephelometer (approx. 5.0 mls of ammonium sulphate solution). 2.5 mls of methanol were added to the solution with stirring. A solution of 0.1 mls of an aqueous 25% w/v glutaraldehyde solution was added at 35° C and the mixture held for 30 minutes with stirring. 1 ml of 7% w/v solution of sodium meta bisulphite in water was added. The solution was diluted with water and frozen in a dry ice-acetone bath and then freeze dried. Scanning electron-microscope studies of the crude dry product showed the product to comprise aggregated spherical particles. The aggregates were about 330–660 nanometers in diameter.

EXAMPLE 6

Example 5 was repeated using bovine serum albumin (4 cm$^3$ 10% pH 4.5) in place of human serum albumin and 20% w/v sodium sulphate (pH 8.3) solution was used in place of the 50% w/v ammonium sulphate solution and the hardening reaction was terminated after 5 minutes. The product was examined by the scanning electron-microscope and was shown to consist of particles of approximately 500 nanometers diameter.

EXAMPLE 7

Example 6 was repeated using 2% casein solution in place of the bovine serum albumin solution and 20% w/v $Na_2SO_4$ adjusted to pH 12.3. After freeze drying a white crumbly powder was obtained/consisting of 120 nanometer particles.

EXAMPLE 8

Example 7 was repeated using 25.6 mls of hydrochloric acid solution (pH 2.1) in place of the 20% w/v sodium sulphate solution, and 1% casein solution (pH 9.5). A white powder was obtained comprising of particles of average size 500 nanometers.

EXAMPLE 9

GENERAL METHOD OF PREPARATION OF NANOPARTICLES WITH GELATIN (i) An aqueous gelatin solution (generally 1–3% w/v) containing a suitable concentration of surfactant (0.5–3.0% w/v) was placed in a glass preparation tube, together with a magnetic stirring bead and the pH was adjusted if required. The system was equilibrated at the desired temperature (generally 35° C) in a water bath.

(ii) A desolvating agent (either 20% w/v aqueous solution of sodium sulphate or 95% v/v ethanol) was added slowly from a burette, with stirring, until the intensity of the scattered light, monitored by frequent nephelometer readings, rose rapidly and the system was permanently faintly turbid. The pH was adjusted where necessary.

(iii) A small amount of a resolvating agent such as ethanol or isopropanol was added until the turbidity disappeared and the intensity of the scattered light decreased to a predetermined point. This point was usually selected so that partial resolvation had occurred and where it was known from earlier experiments that a turbid, flocced system would not form rapidly after the addition of glutaraldehyde. The pH was adjusted if required.

(iv) A laboratory homogenizer fitted with a suitable head, was then introduced into the reaction vessel to provide much stronger agitation.

(v) The hardening agent (a 25% aqueous solution of glutaraldehyde) was added in one aliquot to the system and strong agitation continued for the duration of the hardening process.

(vi) At the end of the hardening process, sodium sulphite or sodium metabisulphite was added to react with excess glutaraldehyde, so that further hardening or aggregation of gelatin particles would not occur. Agitation was continued as in step (v).

(vii) After allowing sufficient time for the sodium sulphite or metabisulphite to react, the systems were frozen in a dry ice/acetone bath and dried overnight in a freeze drying unit. If there was a high concentration of alcohol present, the system was diluted with water before freezing, so that melting would not occur during the initial stages of the drying cycle. Volatile agents, such as ethanol, would be removed during drying.

(viii) Active ingredients could be incorporated at step (i) if they were water soluble or could be solubilized (if water-insoluble) in the surfactant system. Active ingredients could be incorporated in steps (ii) or (iii) if soluble in the alcohols being used as desolvating or resolvating agents. Care must always be taken that the drug will not be precipitated in later stages of the process, so that there is no risk of microencapsulation occurring.

PURIFICATION AND ISOLATION OF THE PRODUCTS

The nanoparticles were separated from solutes and larger pieces of material produced in the reaction by a selective filtration technique.

Using an ultrafiltration system, and a membrane with a molecular weight cut off lower than that of the gelatin, solutes could be removed and the residue thoroughly rinsed to remove traces of reagents. Larger solid by-products of the reaction could be separated from the nanoparticles by filtration through a membrane filter which has a pore size corresponding to the upper size limited desired for the particles. The filtrate, containing the product, could then be frozen and dried as before.

APPEARANCE OF THE PRODUCT

The dried crude products were fine, white powders, which dispersed readily in water to give a "clear solution".

Scanning electron microscope studies of the crude preparations have shown that the powder consists of spherical, fairly uniformly sized particles of approximately 120 nm diameter.

A series of compositions were prepared by the general procedure. The details are as shown in Table I below.

TABLE I

| No | Starting System 10 cm³ unless specified | | Desolvation Agent | cm³ | Resolution Agent | cm³ | Glutaraldehyde cm³ | Conditions | Bisulphite Reaction | Steps of General Method |
|---|---|---|---|---|---|---|---|---|---|---|
| 1 | Gelatin II Polysorbate 20 Phenobarbitone H₂O to | 1% 2% 0.24% 100% | Na₂SO₄ 20% | 7.0 | Isopropanol | 0.8 | 0.6 | Frozen 4 hours | Nil | i-iii Glutaraldehyde added, frozen, dried |
| 2 | Gelatin II Polysorbate 20 Diazepam H₂O to | 1% 3% 0.06% 100% | Na₂SO₄ 20% | | Isopropanol | 0.4 | 0.6 | Frozen 4¾ hours | Nil | As for 5 |
| 3 | System 2 | | Na₂SO₄ 20% | 6.4 | Nil | | 0.6 | Frozen 4¾ hours | Nil | As for 5 |
| 4 | Gelatin II Polysorbate 20 Prednisolone Phosphate H₂O to | 1% 2% 0.3% 100% | Na₂SO₄ 20% | 7.6 | Isopropanol | 1.2 | 0.6 | 35° C for 20 minutes | Na₂S₂O₅ 12% 5 cm³ | i-vii |
| 5 | System 1 | | Na₂SO₄ 20% | 7.1 | Isopropanol | 1.2 | 0.6 | 35° C for 20 minutes | Na₂S₂O₅ 12% 5 cm³ | i-vii |
| 6 | System 2 | | " | 6.5 | " | 1.2 | 0.6 | 35° C for 120 minutes | " | i-vii (stirred magnetically) |
| 7 | System 2 | | " | 6.5 | " | 1.2 | 0.4 | 35° C for 20 minutes | " | i-vii |

The percentage of drug incorporated was measured by U.V. absorption analysis. The product was added to a known amount of water and stirred magnetically. Samples of fluid were withdrawn at selected times and filtered through a 0.45 micron membrane filter. The amount of drug washed out of the product was analysed and the amount of drug remaining in the nanoparticles was calculated. Results are shown in Table II.

TABLE II

| | | Initial Release = Drug Incorporation | | | Subsequent Release | |
|---|---|---|---|---|---|---|
| Sample | Drug | Sample time - Minutes | Mg drug incorporated per 100 mg gelatin | % drug incorporated | Sample time - days | % incorporated drug release |
| 1 | Phenobarbitone | 15 | 5.17 | 21 | 9 16 23 | 0 18 34 |
| 2 | Diazepam | 10 | 1.82 | 31 | 1 2 3 6 8 | 12 21 27 48 56 |
| 3 | Diazepam | 10 | 1.36 | 23 | 1 2 3 6 8 | 20 33 43 70 88 |
| 4* | Prednisolone Phosphate | 300 | 9.79 | 33 | 1 | 21 |
| 5* | Phenobarbitone | 240 | 5.39 | 22 | 3 | 35 |
| 6* | Diazepam | 24 hours | 0.52 | 9 | 2 6 13 | 34 25 76 |
| 7* | Diazepam | 24 hours | 0.67 | 11 | 1 2 6 13 | 11 24 4 34 |

*Determined by dialysis of drug from a solution of the product in place of the filtration method.

We claim:

1. A process of manufacturing particles in the size range from about 10 to about 1000 nanometres which particles comprise a crosslinked matrix of macromolecules of natural origin, which method consists essentially of:
    (a) solvating the macromolecules to form a thermally equilibrated clear solution;
    (b) treating said solution with a desolvating agent until the macromolecules have reached the desolvation region which is the region at which the intensity of scattered light is markedly increased, but before the point at which the solution becomes turbid; and,
    (c) adding an aldehyde hardening agent to the mixture.

2. A process according to claim 1, wherein a biologically or pharmacodynamically active material is added during or after any of the steps a), b) or c).

3. A process according to claim 2, wherein the desolvating region is reached by adding a slight excess of polyvalent anion or polyvalent cation and then adding a small amount of an alcohol, and wherein the active material is added dissolved in the alcohol.

4. A process according to claim 1, wherein the macromolecule is gelatin and the hardening agent is glutaraldehyde.

5. A process according to claim 1, wherein the desolvating agent is chosen from the group consisting of polyvalent anions, polyvalent cations and alcohols.

6. A process according to claim 1, wherein the desolvating region is reached by adding a slight excess of polyvalent anion or polyvalent cation and then adding a small amount of an alcohol.

7. A process according to claim 1, wherein excess hardening agent is removed from the mixture by chemical reaction.

8. A process according to claim 7, wherein the excess aldehyde is removed by reaction with a sulphite.

9. Particles in the size range from about 10 to about 1000 nanometres which particles comprise a crosslinked matrix of macromolecules of natural origin, said particles having been formed by the process of claim 1.

10. Particles according to claim 1 in the range from about 10 to about 500 nanometres.

11. Particles according to claim 1, wherein the matrix of macromolecules of natural origin is selected from the group consisting of serum albumin, collagen, casein, insulin, gum arabic, cellulose derivatives, rosin, zein and mixtures thereof.

12. Particles according to claim 11 wherein the aldehyde is glutaraldehyde.

13. Particles according to claim 12 wherein the matrix of macromolecules is gelatin.

14. Particles according to claim 1, wherein the matrix of macromolecules is gelatin.

15. An injectable composition comprising the particles of claim 9 in a fluid carrier.

16. Particles according to claim 1, wherein the particles comprise a biologically or pharmacodynamically active material supported on or incorporated into the crosslinked matrix.

17. Particles according to claim 16, wherein the active material is selected from the group consisting of phenobarbitone, diazepam, antidepressants, prednisolone phosphate, sodium salicylate, steroids, hormones, atropine and prostaglandins.

18. An injectable composition comprising the particles of claim 16, in a fluid carrier.

* * * * *